United States Patent [19]

Freeman

[11] Patent Number: 4,753,246

[45] Date of Patent: Jun. 28, 1988

[54] EEG SPATIAL FILTER AND METHOD

[75] Inventor: Walter J. Freeman, Berkeley, Calif.

[73] Assignee: The Regents of the University of California

[21] Appl. No.: 845,564

[22] Filed: Mar. 28, 1986

[51] Int. Cl.$^4$ ............................................... A61B 5/04
[52] U.S. Cl. ..................................... 128/731; 364/417
[58] Field of Search ................ 128/731, 732; 364/417, 364/724

[56] References Cited

U.S. PATENT DOCUMENTS

| | | | |
|---|---|---|---|
| 4,416,288 | 11/1983 | Freeman | 128/731 |
| 4,489,390 | 12/1984 | Pareuti et al. | 364/724 |
| 4,590,582 | 5/1986 | Umemura | 364/724 |

Primary Examiner—William E. Kamm
Assistant Examiner—George Manuel
Attorney, Agent, or Firm—Ciotti & Murashige, Irell & Manella

[57] ABSTRACT

Method and apparatus for producing enhanced EEG or MEG information related to a selected brain activity in a subject. The apparatus includes a two-dimensional array of at least about 16 sensors for recording EEG or MEG traces from the subject. Control and test traces recorded before and during an interval in which the brain activity is occurring, respectively, are each decomposed into a series of basis functions which may be analytic components such as temporal frequency components, generated by spectral decomposition of an ensemble average of the recorded traces, or principal components determined by principal component analysis. The control and test traces are then represented as a sum of the products of the individual basis functions times a spatial domain matrix which represents the spatial pattern of amplitudes of that basis function, as measured by the individual sensors in the array. The signals can be extracted by filtering spatially and/or temporally to remove basis function components which are not related to the selected brain activity (clutter), and to remove spatial frequencies inherent in the spatial domain matrices to optimize the contrast between control and and corresponding test matrices, for each selected basis function.

18 Claims, 2 Drawing Sheets

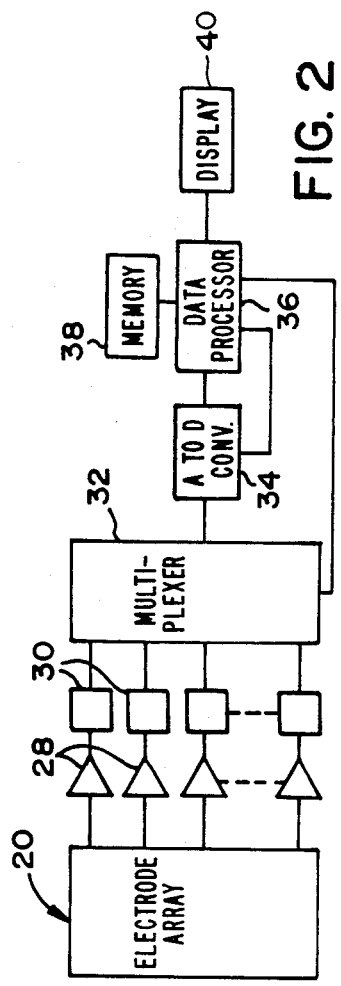
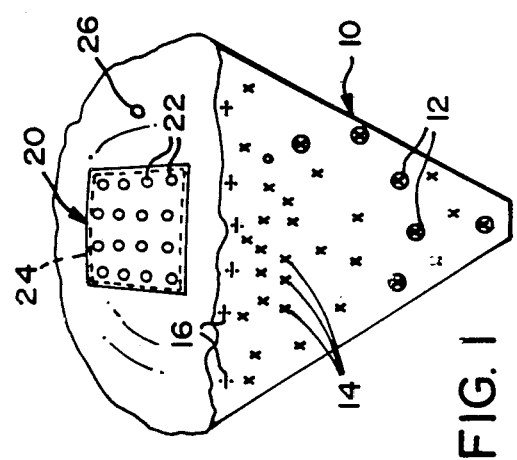
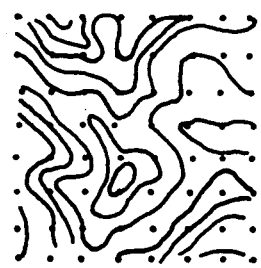
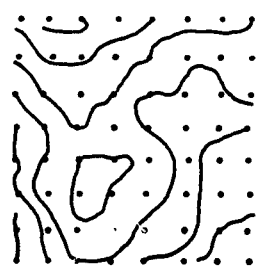
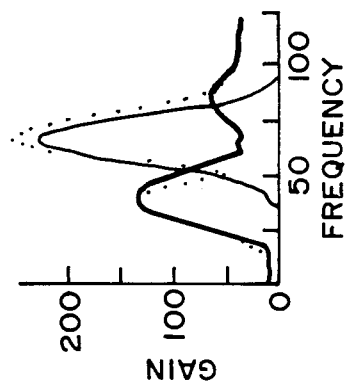
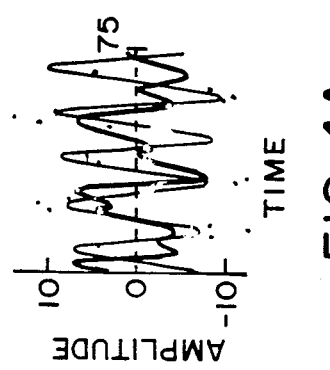

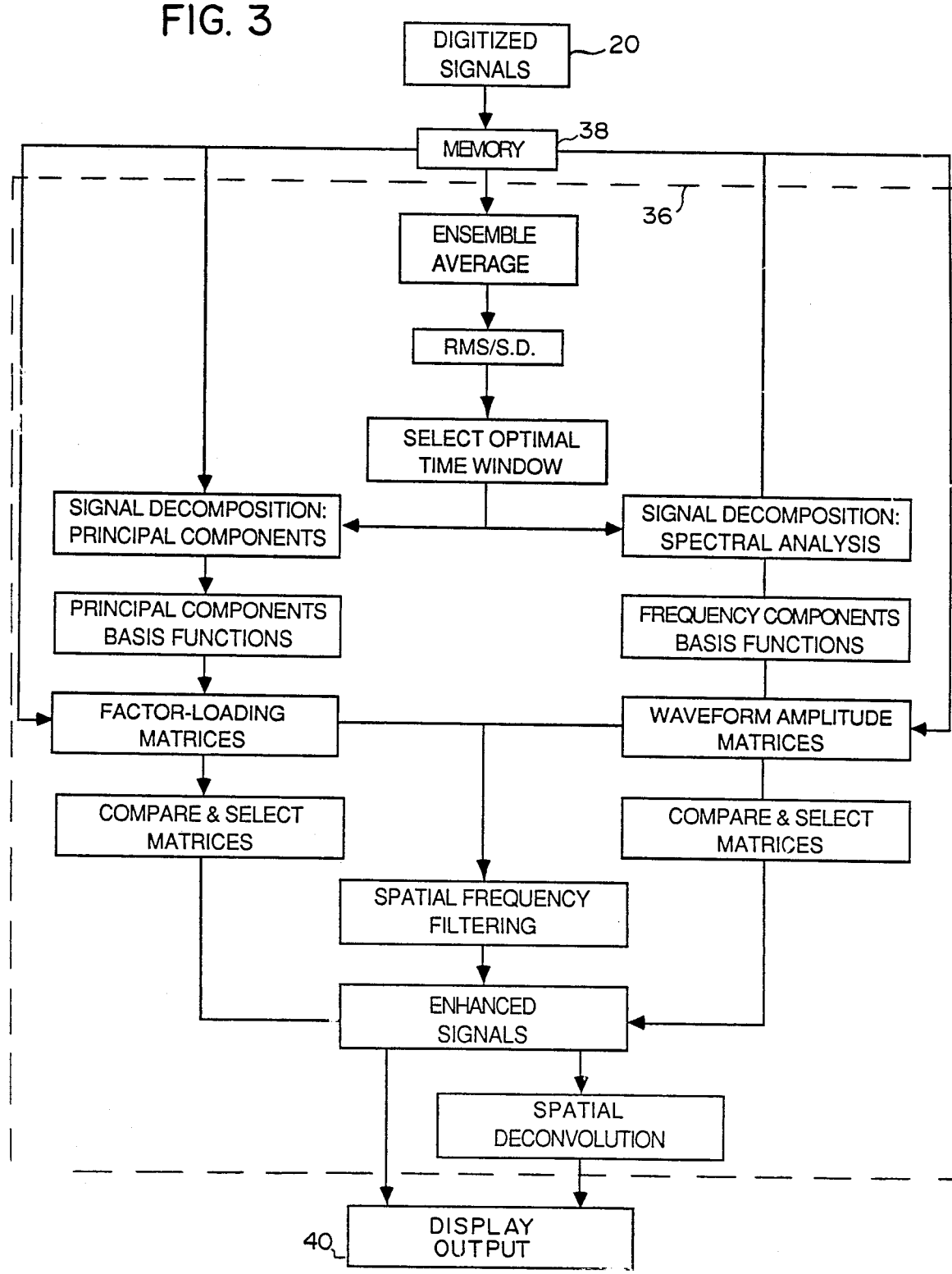

EEG SPATIAL FILTER AND METHOD

This invention was made with Government support under Grant No. MH 00686 awarded by the Department of Health and Human Services. The Government has certain rights in this invention.

FIELD OF THE INVENTION

The present invention relates to methods and apparatus for enhancing brain-activity signals, particularly involving EEG and MEG spatial filtering.

BACKGROUND

There are a number of potentially valuable uses of electroencephalogram (EEG) and magnetoencephalogram (MEG) traces for detecting certain brain states, such as Alzheimer's disease, and for mapping spatial patterns in structures associated with certain behaviorial activity, such as response to certain stimuli, abnormal brain activity, and psychological states and operations.

Heretofore, the potential of EEG in these areas has been limited by inability to identify brain activity signals which are related to a behavioral event of interest, due to masking of signals by clutter and noise, and lack of information about the sites of brain activity. For example, strong electromuscular potentials generated outside the surface of brain mask the presence of 40 Hz signals generated from within brain sites.

One prior art approach for enhancing EEG signal information has been to reduce noise by ensemble time averaging over several time intervals to remove random activity. This does not remove clutter components which are present in each of the averaged time intervals. A brain electrical activity mapping (BEAM) technique, described in U.S. Pat. No. 4,408,616, applies this temporal averaging approach to multisensor arrays, for purposes of brain mapping.

The problem of localizing and determining spatial distribution of brain activity has been addressed by a "software lens" approach, developed by the inventor and described in U.S. Pat. No. 4,416,288. However, spatial and temporal frequency clutter have the effect of blurring the spatial convolution, and thus have limited the power of the method heretofore.

SUMMARY OF THE INVENTION

It is therefore a general object of the present invention to provide a method and apparatus for extracting signals from EEG and MEG traces related to a selected behavioral activity, by separating signal components from noise and clutter components which are unrelated to the selected activity.

One specific object of the invention is to provide such a method and apparatus for identifying, from a multichannel recording taken over a relatively long period which spans the brain activity of interest, a relatively short time interval during which the recording has a maximum spatial coherence and behavioral relevance.

Another specific object is to provide such a method and apparatus for decomposing EEG and MEG traces recorded simultaneously by an array of sensors into a series of basis function components, and removing those components which are not related to the selected behaviorial activity.

Still another object of the invention is to provide such method and apparatus for removing from EEG or MEG traces which are recorded during a behavioral event of interest, spatial frequencies which are not related to the event.

It is yet another object of the invention to provide such method and apparatus for enhancing signal information related to a selected behavioral event, and using the enhanced signal to determine, by spatial deconvolution techniques, the spatial distribution of signal generation related to the event.

In practicing the invention, a two-dimensional array of at least about 16 recording sensors is attached to the brain region of a subject. The sensors in the array are spaced from one another a distance which is substantially no greater than one-half the shortest expected spatial wavelength which is related to a selected behavioral event being investigated in the subject. The area of placement of the array is one in which signals related to the selected activity can be detected by each sensor in the array.

The EEG and MEG traces are simultaneously recorded by the sensors over a period in which the selected behavior is manifested, and a relatively short test interval within the recording period corresponding to the selected event is selected. The traces recorded during the test interval are decomposed into a series of basis functions $B_i$, each of which represents a signal or clutter component which is present to varying degrees in all of the traces recorded by the array sensors in the test interval. For at least one signal basis function $B_j$ that is related to the selected behavioral activity, a corresponding amplitude matrix $A_j$ is determined. This matrix represents the spatial pattern of amplitudes of that basis function in the test interval, measured by the individual sensors in the array. The derived signals, represented in the form:

$$S_a = \Sigma_j A_j B_j,$$

(basis functions), are enhanced for signal information relating to the behavioral event by deletion of clutter and noise.

The time interval which is examined is preferably the interval within the recording period in which the traces show maximum or near-maximum spatial coherence. The interval can be selected by: (a) constructing an ensemble average of the simultaneously recorded traces over the recording period, (b) constructing a moving time window within the recording period, (c) determining for each position of the time window, the ratio of average signal amplitude to the spatial standard deviation of the ensemble average, and (d) selecting each time window which shows a sustained maximum or near-maximum value of such ratio.

In one embodiment of the invention, the traces are decomposed into basis function by first forming an ensemble average of the traces, then decomposing the ensemble average into a series of increasingly less dominant frequency components, typically no more than about five components. In another embodiment, the basis functions are determined directly from the digitized recorded traces, by principal component analysis. Typically only the first one-five principal components are are used.

These components are treated as estimators of brain signals and they are evaluated by use of behavioral correlation. To do this, a series of basis functions and corresponding spatial-pattern matrices representing signals recorded during a control interval, either before or after a selected behavioral event, are also generated. Signal basis functions (which are related to the selected behavioral event) are identified by comparing control and test spatial-pattern matrices for each set of corresponding control and test functions, and selecting those basis functions for which the matrices show a statistically meaningful variance.

Filtering the traces to remove undesired spatial frequencies is carried out, for each basis function, by transforming the associated test and control spatial-distribution matrices into the spatial frequency domain, removing those frequencies which reduce the contrast between the two transformed matrices, and transforming back into the spatial domain, or by equivalent use of convolution in the spatial domain.

The enhanced signal produced by the above methods can be combined with spatial deconvolution techniques described earlier by the inventor in determining the spatial distribution of brain activity related to the behavioral event of interest.

These and other objects and features of the invention will become more fully apparent when the following detailed description of the invention is read in conjunction with the accompanying drawings.

BRIEF DESCRIPTION OF THE DRAWINGS

FIG. 1 represents a volume portion of a brain and a 16-sensor array attached to a skull surface surrounding the brain;

FIG. 2 is a block diagram of apparatus constructed according to the invention;

FIG. 3 is a flow diagram showing signal-processing operations carried out in accordance with the invention;

FIG. 4 shows at left (4A), an example of a spectral decomposition of an ensemble average signal, where the dots indicate the digitized ensemble average, the light curve shows the fitted dominant component, and the dark curve the residual signal after subtracting the dominant component, and at right (4B) the Fourier transform of the dominant (light curve) and residual (dark curve) signals; and FIG. 5 shows a spatial-distribution matrix calculated according to the invention before (5A) and after (5B) spatial filtering to remove spatial frequencies which reduce the contrast between control and test spatial-pattern matrices.

DETAILED DESCRIPTION OF THE INVENTION

The present invention is designed for studying brain wave activity associated with a given behaviorial event. More specifically, the invention uses novel signal enhancement techniques to obtain information about the character and localization of brain activity which occurs during the event. The event may be a specified task, such as a motor activity, which the subject being examined is asked to perform during testing, or it may be a response generated by the subject to certain stimuli. These types of activities would be appreciated, for example, in studying the spatial distribution of nerve cells which are involved in the selected behavior. In another application, the invention is used as an aid in diagnosing nervous disorders whose electrical signal activity has temporal frequency and/or spatial distribution features which are characteristic of the disorder. Here the behavioral activity is one which is associated with the nervous disorder of interest. For example, in studying electrical signal patterns related to dyslexia, the subject activity may involve one of a variety of visual skill tasks.

The general objectives of the invention can be understood, in vrey simplified terms, with reference to a volume region of brain tissue containing nerve cells which are involved in the behavioral or nervous disorder activity of interest. This region, such as the one shown at 10 in FIG. 1, is made up of two very general types of activity generators. The first type, indicated by circled crosses, is made up of nerve cells, such as cells 12, which are involved in the selected behavioral activity. That is, these cells show a characteristic type of electrical activity during this behaviorial event.

The second type of activity generator includes both nerve and muscle cells whose activity is largely independent of the selected behavioral event. The nerve cells in this second group are indicated by crosses, such as at 14. These cells, or some significant portion thereof, contribute brain wave activity which is independent of and masks the activity of the event-related cells, and which is therefore referred to as signal clutter. The muscle cells, which are largely localized outside the surface of the brain region, such as indicated by circles in the figure (cells 16), also contribute clutter to the activity recorded during the behavioral event.

In addition, the recorded traces contain noise from a variety of external and internal sources which also mask signal information related to the event under study. In one aspect, the invention is designed to enhance information generated by the first type of event-related cells, by removing clutter generated by the second type of nerve and muscle cells, and noise. The novel signal enhancement techniques of the invention, and apparatus for carrying out the signal enhancement will be described in Part I below.

In another aspect, the enhanced signals are used to provide information about abnormal disease state, and/or information information about the distribution and localization of brain activity which is related to the behavioral event. These uses are discussed in Part II. Although the invention will be described primarily with respect to EEG signal processing. it is understood that the invention is also applicable to MEG and to brain wave signals generated by optical probe techniques.

I. Signal Enhancement Techniques

A. Trace Recording

The electrical signals from the brain region are recorded by an electrode array 20 which is most simply a rectangular array of discrete electrodes, such as electrodes or sensors, 22. The array preferably includes 64 or more electrodes, although as few as 16 or 32 electrodes may be employed, under circumstances where high signal resolution capability is not required.

The spacing between adjacent electrodes should be no greater than one-half the shortest expected spatial wavelength which is related to the behavioral event without aliasing. For example, if the shortest expected spatial wavelength is 1 cm (spatial frequency equal to 1 cycle/cm), the spacing between electrodes should be no greater than about 0.5 cm. This spacing insures that the array is able to detect essentially all of the important signal information associated with the behavioral event. Provided this interelectrode spacing requirement is met, the electrodes may have an irregular arrangement, although a regular rectangular pattern, such as a regular 8×8 electrode pattern, is preferred.

The diameter of each electrode may be as large as possible consistent with the arrangement of electrodes in the array, while maintaining an effective amount of insulation between adjacent electrodes, in order to reduce electrode noise.

In the electrical hook-up to the subject, the array, such as array 20, is placed on a recording surface so that the area covered by the electrodes is one in which signals related to the behavioral event of interest will be detected by each electrode in the array. Thus, with reference to FIG. 1, array 20 is so positioned that each electrode is responsive to signals from all of the cells, such as cells 12, whose signal activity is related to the behavioral event. The signal area is indicated by dotted lines at 24 in the figure.

The trace recording may be carried out in either a bipolar or monopolar mode, according to conventional techniques. In the monopolar mode, a reference electrode is placed at a remove site such as an earlobe. In the bipolar mode, a reference electrode, such as electrode 26, is placed on the subject recording surface at a distance from the array which is preferably about equal to the "diameter" of the array.

With reference now to FIG. 2, each electrode in array 20 give input to a separate preamplifier 28. The trace detected by each electrode typically varies in amplitude in the range 10-500 microvolts. Each preamplifier is designed to provide high gain amplification for this trace, typically about 10K, while providing high input impedance and low current loading on the electrode. A 64-channel amplifier of the type suitable for an $8 \times 8$ matrix is commercially available.

The preamplifiers may also be used as band pass filters to remove unwanted frequencies. Alternatively, separate band pass filters 30 associated with the preamplifiers may be used. Typically, the filters are designed to remove (e.g., 3 db fall-off) frequencies above about 100-300 Hz, and below about 10 Hz.

The output from the preamplifiers and filters, if used, are coupled to a multiplexer 32. The multiplexer acts to sequentially sample each of the plurality of traces, corresponding to a separate amplifier and filtered analogue signal from each electrode 22, and to output a time division multiplexed signal as a function of these inputs. The sampling rate of the multiplexer is high enough with respect to the temporal rate of change or frequency of the signals being measured to ensure that accurate amplitudes measurements are obtained. Basically, sampling at least once each half cycle is the minimum neede to obtain an accurate measure of the amplitude and rate of change of the signals being sampled. For example, if the highest frequency brain wave signal of interest is 100 Hz, each electrode should be sampled at least once within every 5 msec. It should be noted here that the temporal frequencies of greatest interest rae generally in the 30-60 Hz range. A typical sampling time is 10 $\mu$sec, with a 2 msec interval between read times.

The output of the multiplexer is coupled to an analogue-to-digital converter, which outputs an 8-12 bit digital word for each electrode 22, whose bit state represents the amplitude of a given trace detected by that electrode. Each electrode in the array is sampled, and its output digitized by converter 34 before the sampling process is repeated. In an embodiment having a total of 64 electrodes, for example, the conversion of all 64 sampled signals would be accomplished in a period of about 0.64 msec, if each electrode is sampled and its signal digitized every 10 microsec. The multichannel output from the A/D converter is fed to a data processor 36 which performs the signal processing and enhancing functions described below. The digitized signals may be further corrected for small differences in preamplifier gain, digitally smoothed by averaging over adjacent time samples, and detrended to remove gross features, such as long-period respiratory waves. Another useful smoothing operation is to remove signals which do not correlate well with the average (ensemble average) of the signals. This can be done by cross correlating each signal with the ensemble average signal, and rejecting signals with correlation values below a selected threshold. These additional signal processing operations are performed, in a conventional manner, by the data processor.

Signal data is supplied to and received from the data processor by a memory storage device 38, and the output of the data processor is displayed by a conventional display device 40.

B. Selecting a Time Window

In the usual signal recording procedure, the signals are recorded over a relatively long period of at least several seconds during which the selected behavior event takes place. That is, the recorded signals extend over a period during which maximum signal activity related to the event is occurring, as well as pre- and post-activity periods in which event-related signal activity is suboptimal. Obviously, in order to maximize signal information related to the behavioral event of interest, it is necessary to identify a time interval or window at which such maximal event-related signal activity is occurring.

Behavioral stimuli and responses can provide time markers to place boundaries on time domains that contain signals, but more precise time localization is made with respect to the structure of the brain activity as revealed by the EEG or MEG. As a first step in identifying a desired time window, the traces are averaged at each sampling point over the recording period, to form an ensemble average. This average represents the average of all digitized electrode amplitude values at each time point, e.g., every 2 msec, when analogue-to-digital sampling occurred. The ensemble average is now analyzed over a moving time window, to identify windows having a sustained high ratio of signal amplitude, as determined by the root mean square of the ensemble average amplitudes over the several time points within that time window, to signal variation, as determined by the standard deviation of the amplitudes within that time window. By way of example, if the selected time window is 0.1 seconds, and the values are sampled every 2 msec, a total record of 5 seconds covered by a 0.1 sec moving window has 50 time points in steps of 2 msec. The root means square amplitude and spatial standard deviation are calculated, and the time intervals having sustained high ratios are selected.

The operations just described for calculating an optimal time window are performed by data processor 36, according to conventional signal averaging statistical techniques. These functions are shown in FIG. 3, which illustrates the data processor in dashed lines, and the overall functioning of the data processor in block diagram form. Here it is understood that the data processor operations which are indicated are performed by suitable data processing means. As seen in the upper portion of the figure, digitized, filtered traces from the array (the source of such signals is indicated by box 20, which represents the sensor array and signal amplifying, filtering and digitizing means) are input into the data processor through storage device 38. The stored multichannel signal data is averaged by the data processor to form the ensemble average, root mean square and standard deviation values are calculated, and the rms/sd ratios are compared to identify an optimal time window(s).

Alternatively, an optimal time interval may be selected by visual inspection of the ensemble average, to identify signal regions which show high amplitude values, and minimal amplitude spatial deviation.

As will be seen below, it is generally advantageous in processing event-related traces, to compare the traces from the event-related time period with control traces which are recorded either before or after, but in any case well-separated in time from the behavioral event under study. These traces are obtained from an independent recording in which behavioral event is not present, but some other known behavior, such as rest, waiting, attending, or readiness, is present. The control time window is identified as above, by selecting moving time windows of an ensemble average which show sustained high amplitude and low deviation signal activity. The traces from the control interval are also referred to herein as control traces, and those from the event-related interval, as test traces.

C. Trace Decomposition: Spectral Analysis

According to an important feature of the invention, the test traces are decomposed into a series of basis functions $B_i$, each of which represents a signal or clutter component which is present to various degrees in all of the traces recorded by the array sensors in the selected test interval. Each basis function $B_i$ takes the form of a vector whose amplitudes, representing the the contributions of that vector to the individual traces recorded by the electrode array, is defined by a corresponding amplitude matrix $A_i$. That is, the matrices represent the spatial distribution of amplitudes of the corresponding basis functions, as measured by the individual sensors in the array. The traces $T_a$ recorded by the multiple electrodes can then be expressed in the form:

$$T_a = \Sigma_i A_i B_i \text{ (basis functions)} + \text{noise},$$

where the noise is represented by a residual trace after removing all of the basis functions from the traces.

Two general methods are proposed for decomposing the recorded traces. The first method, which will be described in this section, is based on spectral analysis of an ensemble average. As a first step, the traces from the multi-sensor array are averaged at each sample point, to give an ensemble average of sampled trace values. The ensemble average is then decomposed by Fourier spectral analysis to yield a first basis function $B_1$ which represents the dominant frequency component in the average. Phase, amplitude and frequency values and the amplitude and frequency modulation over time of this component are determined by a least squares deviation methed. Using these calculated values, the dominant frequency component is subtracted from the original ensemble average trace, and the residue trace is again subject to a Fourier transform, to identify the second basis function $B_2$ which represents the next-dominant frequency component in the average (the dominant component in the residue). Phase, amplitude, and frequency values and the amplitude and frequency modulation over time are calculated for the second frequency component in a like manner, and the second dominant component is subtracted from the once-subtracted average, to yield a second residue average. This procedure is repeated, typically 3-5 times, until the residue contains preferably no more than about 10% of the total energy of the original ensemble average.

A general equation for determining V, f and phase P coefficients for the to the ith frequency component $v_i(t)$ in the decomposition procedure is the following:

$$v_i(t) = [1 + AM_i(t-t_m)]V_i \cos [FM_i(t-t_m)t + 2\pi f_i t + P_i),$$

where $t_m$ is the midpoint of the signal time interval, $AM_i$ is the fixed amplitude modulation coefficient, $FM_i$ is the fixed frequency modulation constant (both modulations being linear with time).

The effect of the decomposition steps on a sample ensemble average are illustrated in FIGS. 4A and 4B. The dots in the FIG. 4A curve show the digitized ensemble average. The Fourier transform of this average gives the spectral gains of this data, shown in dots in FIG. 4B. The frequency and phase components for the highest gain were identified, and these values were used to fit a cosine wave to the ensemble average, with a criterion of least squares deviation, using the equation above. The resulting wave is shown as a light curve in FIG. 4A, and the Fourier transform of the wave, as a light curve in FIG. 4B. As seen, the frequency of the dominant component is between about 60-70 Hz. Subtracting the dominant component wave from the average yields the residual average seen in dark lines in FIG. 4A. The residual Fourier signal, which is seen in dark lines in FIG. 4B, indicates the next-dominant frequency component in the spectral decomposition, having a frequency of about 40 Hz.

The FIG. 4A signal was decomposed in this manner to yield five frequency components. Nearly half of the total signal energy was carried in the first component, with the remaining four components, each carrying between 5-10% of the total original energy.

After decomposing the ensemble signal into n basis functions, according to the just-described procedure, the frequency and phase values determined for each function are fixed, and each of the recorded traces from the array electrodes are fitted by linear regression with the sum of n basis functions. Spatial variation in phase is determined by using the sum of sine and cosine functions at each desired frequency. This procedure yields n matrices $A_1 - A_n$ whose values represent the spatial patterns of the amplitude coefficients of each of the $1-n$ basis functions, respectively. In the example above, where the ensemble signal is decomposed into five components, and assuming the electrodes are arranged in an $8 \times 8$ array, the procedure yields five $8 \times 8$ matrices of amplitude coefficients.

The importance of the decomposition method is in reducing complex EEG traces into one or more discrete wave components for which spatial patterns of amplitudes (in the form of the $A_i$ matrices) can be calculated. Viewed from the perspective of the simple brain volume model presented above, the objective of the spectral decomposition is to enhance signal components $B_j$ basis functions which are related to the behavioral event, and remove clutter and noise "background" components.

Coincidentally, the decomposition is intended to enhance spatially coherent signal activity—that is, activity which is recorded simultaneously over the entire electrode array—since cells associated with the selected event will generally be widely distributed throughout the brain volume being monitored and/or located fairly deep within the brain volume, and in either case recorded as spatially coherent signal activity. This activity is in contrast to more localized and and/or shallower brain electrical activity, such as would be produced by cells 14 in FIG. 1, that would not be spatially coherent over the area of the array. Forming the ensemble average, which is the first step in the spectral decomposition method, has the effect of filtering out signal activity which is not spatially coherent, since signal activity localized to a few of the electrodes only will tend to be lost in the averaging step. Also, as indicated above, the time interval being examined has itself been selected for maximal or near-maximal spatial coherence. The ensemble average is now decomposed into several wave components and a residual signal which largely represents random noise. The wave functions, in turn, will show varying degrees of covariance, or correlation with the behavioral event of interest. Those wave components (basis functions) which do not show significant covariance with the behavioral event can be considered as arising primarily from clutter signal activity, and can be discarded. What remains is the one or more signal basis functions $B_j$ which show a significant covariance with the behavioral event and the corresponding spatial distribution matrices $A_j$ which give the spatial distribution of the $B_j$ basis functions over the recording area. The resulting signal, expressed in the form:

$$S_a = \Sigma_j A_j B_j \text{ (basis functions)}$$

has thus been effectively filtered to remove (a) spatially incoherent signal activity (b) signal noise, and (c) spatially coherent clutter which is unrelated to the behavioral event of interest.

The above methodology assumes that the basis functions $B_j$ which are most related to the selected behavioral event can be identified. There are three general approaches to this problem. The first, and simplest approach, is to assume that only the first or first few dominant components are event-related, and discard those less dominant components generated by the decomposition method. Since the first dominant component will typically contain about 50% of the total signal energy, it is reasonable to assume that most interesting signal information will be found here.

A second and more comprehensive approach is to determine the statistical correlation between each basis function and the event of interest. This is done, according to a preferred method of the invention, by recording above-described control EEG traces. The control traces are then decomposed in a manner similar to the above, to generate a series of successively less dominant basis functions $B'_i$ and their associated spatial-distribution matrices $C_i$. The test $A_i$ and corresponding control $C_i$ for the each of the first through nth dominant component are now compared for statistically meaningful variance or contrast, according to known statistical methods. The signal basis functions $B_j$ which are most related to the behavioral event are, of course, those for which such variance is found.

A third method for determining event-related (signal) basis functions $B_j$ relies on the ability to identify event-related frequency components which occur consistently in a large sampling of subjects. Here identification of relevant signal components in a test subject is based on the finding that such event-related components occur consistently in a relatively large population of subjects. This method would be suitable, for example, in a clinical setting in which signal recordings related to the same event are recorded for a large number of subjects.

The signal decomposition procedures just described are performed by suitable signal processing means contained in the data processor. As seen in the flow diagram in FIG. 3, the ensemble average signal used in identifying the selected time window(s) is spectrally decomposed to form a series of basis functions, associated spatial distribution matrices are constructed for both test and control basis functions, and the test and control matrices are examined for statistical correlation, to determine the test signal basis functions which are related to the behavioral event of interest. The enhanced signal can now be constructed and displayed in a system output 40.

D. Trace Decomposition: Principal Components

The basis functions used in EEG signal information enhancement, in accordance with the invention, can also be generated by principal component analysis. As a general statistical procedure, this method is used to transform multivariate data from a real-space coordinate system into a system of principal components which are characterized by varying degrees of covariance among the data. The principal-components are vectors which form the basis functions $B_i$ of the decomposed signals, and the corresponding covariance matrices are the spatial-pattern matrices of factor loadings $A_i$ associated with each vector.

In the decomposition method involving n digitized signals, the n amplitude values at each time point in the signal window are plotted in n-dimensional space, generating an n-dimensional ellipsoid. This ellipsoid has its greatest elliptical axis in the direction of maximum variance, which defines the first principal component $B_1$ basis function in the transformation space. the covariance matrix $A_1$, which represents the spatial pattern of the n signal amplitudes along the first principal component is then calculated by conventional statistical methods. The reader is referred to general texts on methods of multivariate analysis.

The second principal component $B_2$ basis function is similarly identified as the second greatest elliptical axis in the n-dimensional ellipsoid, and represents the axis of second greatest variance among the data points. The associated covariance matrix $A_2$, representing the spatial distribution of signal points along the second principal axis is determined, and the procedure is repeated several times to generate a series of principal components $B_i$ basis function and corresponding spatial pattern matrices $A_i$.

In practice, and according to an important feature of the method, the degree of covariance falls off rapidly beyond the first few principal components, so that the signal can be quickly reduced to one or a few principal components, and non-covariant information can be largely eliminated. This feature corresponds roughly to the spectral decomposition approach discussed above, where an ensemble average signal is reduced to one or a few principal frequency components, and signal information arising from noise and low-level clutter drops out as residual signal. Further, it is noted that spatial incoherence, which is reduced in the spectral decomposition method by ensemble averaging, is inherently reduced in decomposing the signal into principal components. This is because n-space data points which are not spatially coherent tend to distribute within the n-dimensional volume which defines the principal components.

Also analogous with the above spectral decomposition approach, it is further useful, in removing clutter components from the recorded traces, to remove basis functions (i.e., principal components) which are not statistically related to the behavioral event of interest. This may be done, as above, by determining a set of spatial distribution matrices $A_i$ associated with traces recorded during a test interval, and a corresponding set of matrices $C_i$ associated with traces recorded during a control interval in which the behavioral event is not occurring. Those principal signal components $B_j$ basis function whose corresponding $A_j$ and $C_j$ matrices show a statistically meaningful variance are then identified as related to the behavior of interest.

Alternatively, the desired principal components can be determined empirically, by selecting the first one or few principal components, or from the results of signal analysis on a large population of subjects. Yet another option is varimax rotation of selected principal components.

The resulting signal, expressed in the form:

$$S_a = \Sigma_j A_j B_j \text{ (basis functions)}$$

has thus been effectively filtered to remove (a) spatially incoherent trace activity (b) spatially coherent clutter which is unrelated to the behavioral event of interest, and (c) noise.

Means in the data processor for performing the principal component analysis just described are shown in the block diagram in FIG. 3. As seen here, digitized signal information from the signal source is converted by principal component analysis to a set of basis functions, covariance matrices for both test and control basis functions are determined, and the matrices are compared by statistical analysis to identify principal components which are related to the event of interest. The enhanced signal is then displayed at output device 40.

Of the two decomposition methods which are described above, the spectral decomposition approach is generally more powerful in terms of enhancing signal information related to a behavioral event. The spectral decomposition is particularly suited to signal analysis involving a large number—e.g., 64 or more—recorded signals. However, the principal component analysis may allow signal decomposition of relatively small arrays—e.g., containing only 16 recorded traces—with better statistical accuracy than the spectral decomposition method.

E. Spatial Frequency Filtering

Each matrix $A_i$ associated with a basis function $B_i$ in the decomposed signals provides, as indicated above, a spatial map of the amplitude pattern of the basis vector over the area of the sensor array. This map shows higher spatial frequency components, corresponding to more closely grouped frequency "generators", in the form of more closely spaced contour lines, and lower frequency components, in the form of more widely spaced contour lines. Generally, higher spatial frequencies are associated with more localized and/or shallower brain electrical activity, and also electromuscular signals generated outside the brain. Lower spatial frequencies, on the other hand, are indicative of relatively widely distributed signal activity and/or activity from deeper within the brain. The behavioral events of interest which are studied according to the method of the invention are usually associated with these lower spatial frequencies. The higher spatial frequencies, and perhaps certain low spatial frequencies, may thus be predominantly spatial clutter components, analogous to temporal frequency clutter components which reduce signal information related to the brain activity of interest. This section is concerned with methods of signal enhancement which involve filtering out such clutter frequency components.

FIG. 5A shows a contour map of a typical spatial distribution matrix $A_i$ determined as above. Although the contour map provides a rough picture of the spatial frequency distribution inherent in the matrix, the spatial frequency components are preferably identified by subjecting the matrix to a two-dimensional spatial Fourier transform, to generate the corresponding spatial frequency matrix. A low pass filter, such as a 4th-order exponential filter (Gonzales, R. C. and Wintz, P. (1977) Digital Image Processing, Addison-Wesley, Reading, MA.) is applied to the matrix to remove higher spatial frequency components above the spectral range accessible to cell generators associated with the behavioral event of interest. Typically, the amount of energy removed from the total energy in the components is between about 10–40%. The inverse transform is then applied to take the filtered data back to the spatial domain. Here it is noted that the filtering operation may also be carried out directly on the spatial distribution matrices, using known convolution techniques which are equivalent in effect to the frequency transform, filtering, and inverse transform steps just described. The spatial frequency filtering operations are performed by the data processor, as indicated in FIG. 3, according to known signal processing methods.

FIG. 5B shows the contour map of the Figure 5A matrix after removing higher spatial frequency components. As seen, the filtering operation has smoothed the contours in the high frequency regions, without changing the overall spatial distribution pattern of the amplitude values in the unfiltered matrix.

In the above method, it is assumed that a spatial frequency filter cutoff which will provide good enhancement of recorded signals is known. In a preferred filtering method, an optimal frequency cutoff is determined by statistical correlation with a filtered control matrix. In this procedure, a selected test transformed matrix and the corresponding transformed matrix determined from control traces are each filtered by a series of low-pass filters that progressively limit the upper spatial frequencies which are passed. The series of filter operations progressively smooth the spatial contour map, with the more closely spaced contours being smoothed first. At each stage in the filter operation, the filtered matrices are compared to determine how the spatial filter operation has affected the degree of correlation between the two matrices. A typical plot of the degree of correlation as a function of spatial frequency shows a peak correlation at one spatial frequency, e.g., about 0.5 cycles/mm, and a progressive loss of correlation at lower filter cut-off frequencies. This peak defines the optimal low-pass filter frequency for the spatial filter.

A particular advantage of spatial frequency filtering is that the spatial filter removes most of the EMG components—which are generally associated with more closely spaced frequency generators near the scalp—and therefore allows for unambiguous detection of recorded signal activity in the 20–80 Hz range. Another use of the spatial filter is to refine the basis function selection procedure. To illustrate, once an optimal spatial filter frequency has been determined, the spatial filter can be applied to amplitude matrices associated with basis functions $B_i$ which were previously rejected as clutter, but which, after spatial filtering, may show matrix correlation with brain activity for that particular frequency component. This method provides greater refinement of the enhanced brain-activity signal in terms of the basis functions which contribute to the signal.

II. Applications

A. Diagnosing Neurological Disorders

One general application of the invention is its use in identifying signal information which is related to neurological disorders and in diagnosing disorders based on characteristic brain activity signals. The application relies on the ability of the method to extract from complex EEG or MEG traces, signal information which is predominantly related to some behavioral event.

As one example, there is evidence that Alzheimer's disease is associated with a 40 Hz signal which occurs under defined behavioral conditions. The characteristic signal is difficult to detect by conventional EEG signal processing techniques, due to electromuscular activity which is in the same general frequency range, and also relatively strong due to its proximity to the recording electrodes. In the present invention, the electromuscular activity can be filtered out primarily in the form of spatial clutter, since its spatial frequencies will be higher than those of more delocalized and deeper brain activity in the same temporal frequency range.

In a typical diagnostic procedure, EEG traces from a large array of sensors are decomposed to remove noise and temporal frequency clutter above and below the temporal frequency of interest, here 40 Hz. The spatial-pattern matrix of the 40 Hz basis component(s) is then spatially filtered to remove higher spatial frequencies, including those associated with localized electromuscular activity. The enhanced signal gives a relatively unambiguous reading of the disorder.

Similarly, the method can be used to identify signal components which are characteristic of a neurological disorder which one wishes to be able to diagnose on a routine basis by EEG or MEG recordings. As an example, it would be desirable to be able to diagnose dyslexia in young children by EEG recording techniques. Here one would identify a behavioral event, such as a visual task, which is likely to be manifested in certain brain activity when the disorder is present. Control and test recordings from a number of subjects would be processed, according to the invention, first to remove noise and secondly to identify temporal frequency components which appear to correlate with the selected behavioral event. This identification is made on the basis of correlation between control and test spatial-pattern matrices. After identifying the basis functions of interest, the corresponding matrices are spatially filtered, to enhance further the contrast between control and test signal information. The resulting signal is freed of noise and spatial and temporal clutter. The signal information from a large group of control and affected subjects are compared to determine whether any strong disease correlations exist. It may be necessary, of course, to study signal information recorded from different recording sites to determine the optimal sensor position for detecting disorder-related signal differences.

Another application involves the use of the signal enhancement method to investigate the effects of drugs on certain mental states. Studies of this type would be desired, for example, at establishing drug dosage and duration parameters, pharmacokinetic or drug effects on certain behavioral activity, as reflected by a change in the signal activity associated with a selected behavioral event.

B. Brain Mapping

A second general application of the invention is in localizing and determining the spatial distribution of brain activity associated with certain brain functions, such as cognitive thought. The method is based on the earlier "software lens" concept described by the inventor in U.S. Pat. No. 4,416,288. Briefly, the concept there was to employ some simplifying assumptions about the nature of signal generation in the brain to obtain a spatial convolution matrix relating the spatial distribution of recorded signals with the site of the signal generators.

The early applications of the software lens approach involved EEG traces that had substantial temporal frequency and spatial clutter components. It can be appreciated that both types of clutter would have the effect of blurring the spatial convolution, since the generation sites of spatial and frequency signal components which are extraneous to the signal of interest would be averaged into the convolution matrix. In the present method, the filtering operations for removing temporal frequency and spatial clutter are combined with the software lens to produce a more accurate image of brain activity locations and spatial distribution. Recent experiments performed by the inventor on EEG localization in the rabbit olfactory bulb indicate that the combined method can yield a much different, and more accurate picture of spatial distribution of brain activity than the software lens approach alone.

While preferred embodiments and uses of the invention have been described, it will be apparent that various changes and modifications can be made without departing from the invention.

It is claimed:

1. A machine-implemented method for enhancing EEG or MEG information related to a selected behavioral activity in a subject, comprising attaching to the subject, a two-dimensional array of at least about 16 sensors for recording EEG or MEG traces from the subject, where the sensors are spaced from one another a distance which is substantially no greater than one-half the shortest expected spatial wavelength which is related to the selected behavioral activity, and where the area of placement of the array is one in which signals related to the selected activity can be detected by each sensor in the array, recording test EEG or MEG traces by the sensors over a period in which the selected behavior is manifested, selecting a test time interval within the recording period when such activity is occurring;

decomposing the recorded traces into a series of basis functions $B_i$, each of which represents a signal or clutter component which is present to various degrees in all of the traces recorded by the array sensors in the selected test interval, determining, for at least one signal basis function $B_j$ that is related to the selected behavioral activity, an amplitude matrix $A_j$ which represents the spatial pattern of amplitudes of that basis function, as measured by the individual sensors in the array, in the selected test interval, and representing test signals $S_a$ recorded during the test interval by the array of sensors in the form:

$$S_a = \Sigma_j A_j B_j \text{ (basis functions)}.$$

2. The method of claim 1, wherein the two-dimensional array includes a substantially rectangular array of at least about $8 \times 8$ sensors.

3. The method of claim 1, wherein the modal spacing between adjacent sensors is between about 0.5 mm and 2.0 cm.

4. The method of claim 1, wherein selecting the test time interval includes the steps of (a) constructing an ensemble average of the recorded signals over the recording period, (b) constructing a moving time window within the recording period, (c) determining for each position of the time window, the ratio of average signal amplitude to the spatial standard deviation of the ensemble average, and (d) selecting each time window which shows a sustained maximum or near-maximum value of such ratio.

5. The method of claim 1, wherein said decomposing includes the steps of (a) constructing an ensemble average of the recorded traces over the selected time interval and (b) performing a spectral decomposition of the ensemble average trace to obtain a series of such basis functions $B_i$ which represent temporal frequency components of the ensemble average.

6. The method of claim 5, wherein performing the spectral decomposition includes (a) determining a first basis function $B_1$ representing the dominant frequency component in the ensemble average and having estimated frequency, phase, and amplitude values, (b) subtracting the $B_1$ basis function frequency component from the ensemble average to obtain a residual ensemble average, and (c) repeating the determining and subtracting steps to obtain a series of basis functions $B_2 - B_n$ representing successively less dominant frequency components, until the residual ensemble average remaining after removing the $B_n$ basis function contains about 10% or less of the total energy of the original ensemble average.

7. The method of claim 1, wherein said decomposing includes using principal component analysis to generate a series of basis functions $B_j$ which represent the dominant components of signal values over the selected time interval.

8. The method of claim 1, wherein the signal basis functions $B_j$ which are related to the selected brain state are determined by the steps of:

recording control EEG or MEG traces by the sensors during a control time interval which occurs either before or after such brain activity, decomposing the control traces into a series of basis functions $B'_i$, each of which (a) represents a signal component which is present to various degrees in all of the traces recorded by the array sensors in the control time interval, and (b) corresponds to a $B_i$ basis function in the test signals, determining, for each $B_i$ basis and corresponding $B'_i$ basis function, an associated $A_i$ and $C_i$ amplitude matrix, respectively, which represents the spatial pattern of amplitudes of the associated basis function, as measured by the individual sensors in the array during the test and control intervals, respectively, and selecting from among the basis functions $B_i$, those signal basis function $B_j$ for which the associated amplitude matrix $A_j$ shows a statistically meaningful variance with the corresponding amplitude matrix $C_j$.

9. The method of claim 1, which further includes operating on one or more of the $A_j$ amplitude matrices to remove spatial frequencies which are substantially unrelated to the selected behavioral activity.

10. The method of claim 9, wherein said operating includes transforming the amplitude matrix to the spatial frequency domain, generating a spatial frequency matrix, filtering the spatial frequency matrix to remove spatial frequencies which are not associated with the selected brain activity, and transforming the filtered spatial frequency matrix back to the spatial domain, or performing the equivalent convolution on the spatial-distribution matrix.

11. The method of claim 9, wherein the spatial frequencies which are substantially unrelated to the selected behavioral activity are identified by the steps of:

recording control EEG or MEG traces by the sensors during a control interval which occurs either before or after such brain activity, decomposing the control traces into a series of basis functions $B'_i$, each of which (a) represents a signal or clutter component which is present to various degrees in all of the traces recorded by the array sensors in the control time interval, and (b) corresponds to a $B_i$ basis function in the test traces, determining, for each $B_i$ and corresponding $B'_i$ basis function, an $A_i$ and $C_i$ amplitude matrix, respectively, which represents the spatial pattern of amplitudes of the associated basis function, as measured by the individual sensors in the array during the test and control intervals, respectively, and measuring the degree of statistical correlation between the $A_i$ and corresponding $C_i$ matrices as a function of spatial frequency cutoff, to identify those spatial frequencies which optimize the contrast between the two matrices.

12. The method of claim 1, for recovering a spatial pattern of cell-generated signals within the brain of the subject which are related to the selected behavioral activity, and which are responsible for the traces recorded on the subject by the array of sensors, which further includes computing a transform function which relates the enhanced signal $S_a = \Sigma_j A_j B_j$ (basis functions) to signal generation within the brain during the selected brain activity, according to the laws of conduction in a volume, and computing the product of the signal $S_a$ and the inverse transform function, to generate such spatial pattern of cell-generated signals.

13. A machine-implemented method for enhancing EEG or MEG information related to a selected brain activity in a subject, comprising:

attaching to the subject, a two dimensional array of at least about 16 sensors for recording EEG or MEG traces from the subject, where the sensors are spaced from one another a distance which is substantially no greater than one-half the shortest expected spatial wavelength which is related to the selected behavioral activity, and where the area of placement of the array is one in which signals related to the selected event can be detected by each sensor in the array, recording control and test EEG or MEG traces by the sensors during control and test time intervals, respectively, which occur before and during such selected brain activity, respectively, decomposing the recorded test and control signals into a series of basis functions $B_i$ and $B'_i$, respectively, each of which represents a signal or clutter component which is present to various degrees in the test and control traces, respectively, recorded by the array sensors in the selected test or control intervals, determining, for each $B_i$ and corresponding $B'_i$ basis function, an $A_i$ and $C_i$ amplitude matrix, respectively, which represents the spatial pattern of amplitudes of the associated basis function, as measured by the individual sensors in the array during the test and control intervals, respectively, selecting from among the basis functions $B_i$, those signal basis functions $B_j$ for which the associated amplitude matrix $A_j$ shows a statistically meaningful variance with the corresponding amplitude matrix $C_j$.

representing test signals $S_a$ recorded by the sensors in the form:

$$S_a = \Sigma_j A_j B_j \text{ (basis functions)}.$$

14. The method of claim 13, which further includes measuring the degree of statistically correlation between the $A_j$ and corresponding $C_j$ matrices as a function of spatial frequency cutoff, to identify those spatial frequencies which reduce the contrast between the two corresponding matrices, filtering the $A_j$ matrices to remove the identified spatial frequencies, producing the corresponding filtered matrix $FA_j$, and representing test signals $S_a$ recorded by the electrodes in the form:

$$S_a = \Sigma_j FA_j B_j \text{ (basis functions)}.$$

15. An apparatus for providing enhanced EEG or MEG information related to a selected behavioral activity in a subject, comprising:

a two-dimensional array of at least about 16 sensors for recording EEG or MEG traces from the subject, where the sensors are spaced from one another by a distance which is substantially no greater than one-half the shortest expected spatial wavelength which is related to the selected behavioral activity, and where the area of placement of the array is one in which signals related to the selected event can be detected by each sensor in the array, means for recording test EEG or MEG traces by the sensors during a test interval in which the selected brain activity is occurring, and means for filtering the recorded traces to remove clutter components which are unrelated to such behavioral activity, said filtering means including means for decomposing the test traces into a series of basis functions $B_i$, each of which represents a signal or clutter component which is present to various degrees in all of the signals recorded by the array sensors in the test interval, and means for determining, for at least one signal basis function $B_j$ that is related to the selected brain activity, an amplitude matrix $A_j$ which represents the spatial pattern of amplitudes of that basis function, as measured by the individual sensors in the array, thereby to generate filtered signals recorded during the test interval by the array of sensors in the form:

$$S_a = \Sigma_j A_j B_j \text{ (basis functions)}.$$

16. The apparatus of claim 15, which is used to record traces both before and during the selected behavioral activity, and to generate both control and test basis functions $B_i$, $B'_i$, respectively, and associated spatial-pattern matrices $A_i$ and $C_i$, which further includes means for measuring the extent of statistical variance between $C_i$ and the corresponding $A_i$, to determine which of the $B_i$ basis functions is related to the selected brain activity signal and which is not related and is clutter.

17. The apparatus of claim 16, which further includes means for spatially filtering $A_i$ to enhance the contrast between $A_i$ and the corresponding $C_i$.

18. The apparatus of claim 17, for use in recovering a spatial pattern of cell-generated signals within the brain of the subject which are related to the selected behavioral activity, and which are responsible for the signals recorded on the subject by the array of sensors, which further includes means for computing a transform function which relates the enhanced signal $S_a = \Sigma_j A_j B_j$ (basis functions) to signal generation within the brain during the selected brain activity, according to the laws of conduction in a volume, and means for computing the product of the inverse of the signal $S_a$ and the inverse transform function, to generate such spatial pattern of cell-generated signals.

* * * * *